(12) United States Patent
Zarda et al.

(10) Patent No.: US 7,740,659 B2
(45) Date of Patent: Jun. 22, 2010

(54) INSERT FOR NUCLEUS IMPLANT

(75) Inventors: Brett R. Zarda, Providence, RI (US); Michael J. O'Neil, West Barnstable, MA (US); Mark T. Hall, Bridgewater, MA (US)

(73) Assignee: DePuy Spine, Inc., Raynham, MA (US)

( * ) Notice: Subject to any disclaimer, the term of this patent is extended or adjusted under 35 U.S.C. 154(b) by 399 days.

(21) Appl. No.: 11/427,411

(22) Filed: Jun. 29, 2006

(65) Prior Publication Data

US 2008/0009943 A1    Jan. 10, 2008

(51) Int. Cl.
A61F 2/44    (2006.01)
(52) U.S. Cl. .................................... 623/17.11
(58) Field of Classification Search ............ 623/17.11, 623/17.13, 17.16
See application file for complete search history.

(56) References Cited

U.S. PATENT DOCUMENTS

| | | | |
|---|---|---|---|
| 4,892,545 A | 1/1990 | Day et al. | |
| 5,263,953 A * | 11/1993 | Bagby | 606/279 |
| 5,306,310 A * | 4/1994 | Siebels | 623/17.13 |
| 6,245,107 B1 | 6/2001 | Ferree | |
| 6,371,990 B1 | 4/2002 | Ferree | |
| 6,592,625 B2 | 7/2003 | Cauthen | |
| 6,648,920 B2 | 11/2003 | Ferree | |
| 6,883,520 B2 | 4/2005 | Lambrecht et al. | |
| 6,974,479 B2 | 12/2005 | Trieu | |
| 7,297,162 B2 * | 11/2007 | Mujwid | 623/17.13 |
| 7,309,357 B2 * | 12/2007 | Kim | 623/17.13 |
| 2002/0183847 A1 * | 12/2002 | Lieberman | 623/17.11 |
| 2003/0018390 A1 * | 1/2003 | Husson | 623/17.16 |
| 2003/0181979 A1 * | 9/2003 | Ferree | 623/17.11 |
| 2004/0225361 A1 * | 11/2004 | Glenn et al. | 623/17.12 |
| 2004/0249463 A1 * | 12/2004 | Bindseil et al. | 623/17.16 |
| 2005/0038519 A1 | 2/2005 | Lambrecht et al. | |
| 2005/0113928 A1 | 5/2005 | Cragg et al. | |
| 2005/0125066 A1 | 6/2005 | McAfee | |
| 2005/0283246 A1 | 12/2005 | Cauthen et al. | |
| 2006/0052872 A1 * | 3/2006 | Studer et al. | 623/17.13 |
| 2006/0190083 A1 * | 8/2006 | Arnin et al. | 623/17.13 |
| 2006/0200239 A1 * | 9/2006 | Rothman et al. | 623/17.13 |

FOREIGN PATENT DOCUMENTS

WO    WO-2005/092248    10/2005

* cited by examiner

*Primary Examiner*—Thomas C Barrett
*Assistant Examiner*—Nicholas Woodall
(74) *Attorney, Agent, or Firm*—Nutter McClennen & Fish LLP

(57) ABSTRACT

Methods and devices are provided for replacing a nucleus of a spinal disc, and in particular for preventing nucleus disc replacement expulsion. The nucleus of a spinal disc can be removed from the annulus by forming a small opening in the annulus. Once the nucleus is removed, one or more insert devices can be implanted within the annulus of a spinal disc and they can be mated to one or both endplates of the adjacent vertebrae. The insert(s) is configured to interact with a nucleus disc replacement implant to prevent expulsion of the implant from the annulus.

11 Claims, 9 Drawing Sheets

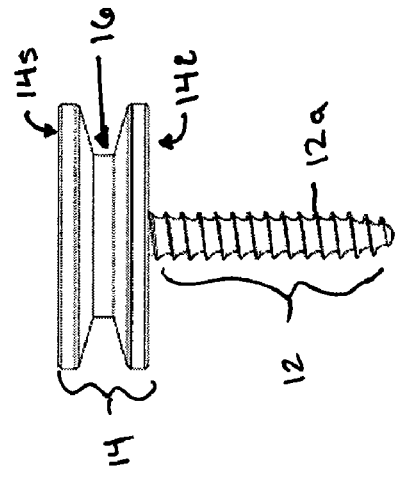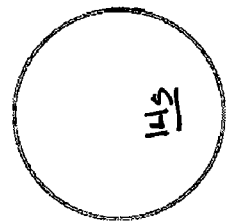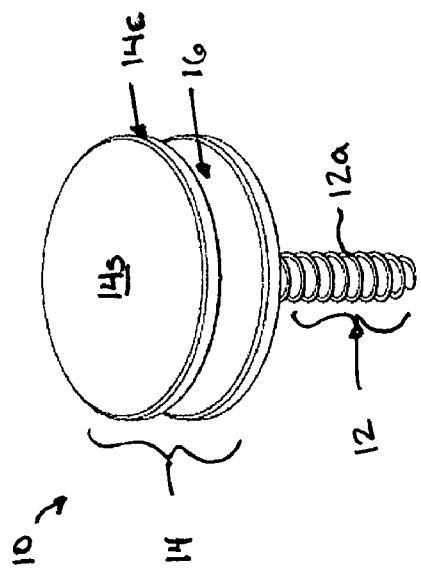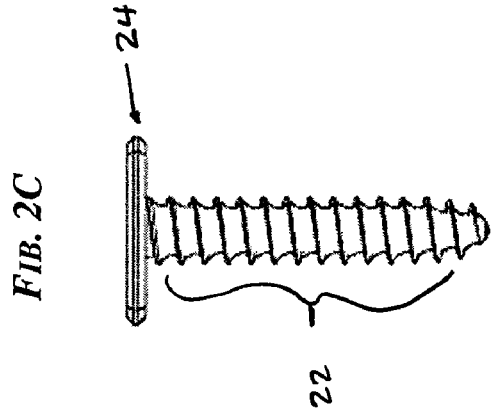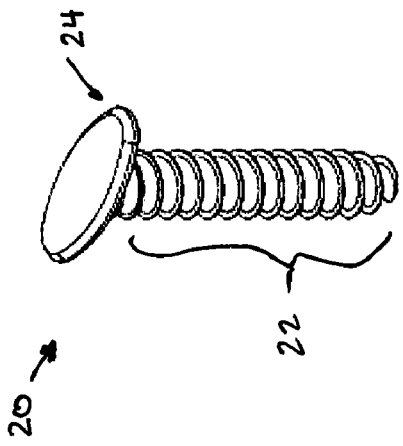

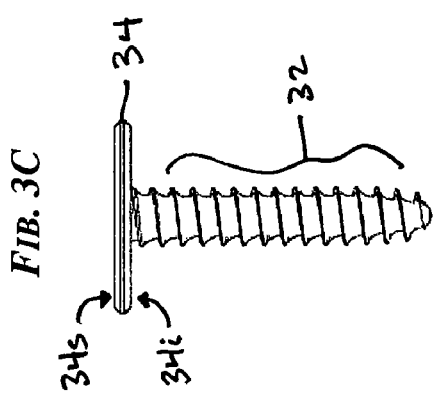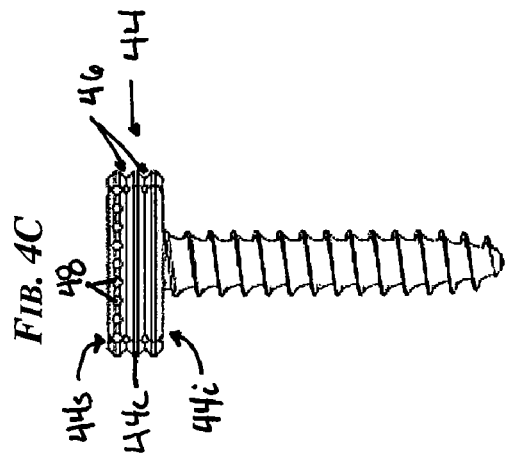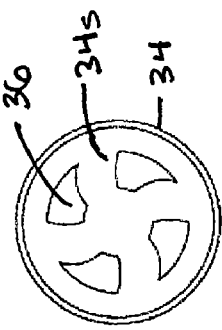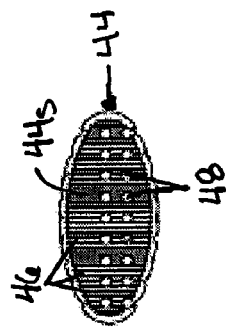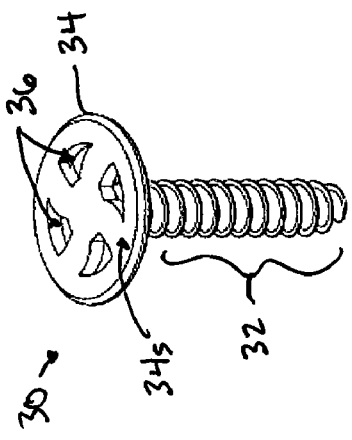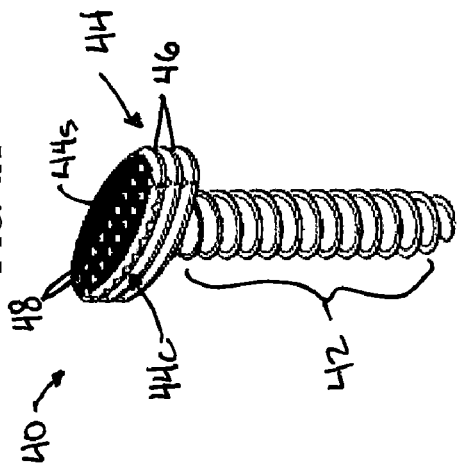

INSERT FOR NUCLEUS IMPLANT

FIELD OF THE INVENTION

The present invention relates to methods and devices for replacing a nucleus of a spinal disc.

BACKGROUND OF THE INVENTION

A spinal disc is composed of two main parts, a gel-like inner portion called the nucleus pulposus, and a tough outer portion called the annulus fibrosus. The annulus is similar to a radial tire surrounding the nucleus. In a healthy disc, the nucleus is contained, and for the most part, centered within layers of the annulus, allowing for even distribution of pressures thereby providing cushioning to the adjacent vertebrae surrounding the disc.

An artificial disc (also called a disc replacement, disc prosthesis or spine arthroplasty device) is a device that is implanted into the spine to imitate the functions of a natural disc (carry load and allow motion). There are many artificial disc designs classified into two general types: total disc replacement (TDR) and nucleus disc replacement (NDR). As the names imply, with a TDR, all or most of the disc tissue is removed and a replacement device is implanted into the space between the vertebra. With an NDR, only the center of the disc (the nucleus) is removed and replaced with an implant. The outer part of the disc (the annulus) is not removed. NDR surgery offers certain benefits compared to TDR. Since an NDR device is designed to replace only the nucleus of the disc, the procedure is less time consuming and posses less risk and maintains the functionality of surrounding structures.

One of the primary hurdles an NDR device has to overcome is the ability to stay within the annulus of the disc. In order to closely mimic the native nucleus, most NDR devices are made of soft and pliable plastic-like (biopolymer) materials. One such material is called hydrogel, which expands as it absorbs water. The device is placed into the nucleus cavity of the disc and hydrates to expand and fill the cavity. The device is flexible or compressible and by this means, allows motion, much like a natural disc nucleus. In particular, the device can elastically deform during normal activities (axial loading, flexion, extension). As a result, the device can potentially squeeze out of the opening(s) formed in the annulus and used to introduce the NDR into the annulus. Another issue is that the containment wall of the NDR is often a degenerated annulus that has existing fissures or will develop fissures in which the NDR device can expulse over time.

Accordingly, there remains a need for improved methods and devices for replacing a nucleus of a spinal disc, and in particular for preventing nucleus disc replacement expulsion.

SUMMARY OF THE INVENTION

The present invention generally provides methods and devices for replacing a nucleus of a spinal disc. In one exemplary embodiment, a vertebral body insert device is provided and includes an insert body having a bone-engaging portion configured to engage bone to maintain the insert body in a substantially fixed position relative to the bone, and a mating portion adapted to mate with a nucleus implant. The mating portion can be sized and shaped for positioning within an annular space defined by an annulus of a spinal disc such that the mating portion has a size that is less than a size of the annular space.

While the bone-engaging portion can have a variety of configurations, in one exemplary embodiment the bone-engaging portion can be adapted to penetrate an endplate of a vertebral body. For example, the bone-engaging portion can be in the form of a shank that is adapted to be disposed within a bone hole for engaging bone. For example, the shank can be threaded for mating to bone. In other embodiments, the bone-engaging portion can be in the form of at least one wire extending from the mating portion and having a terminal end adapted to engage bone. In another embodiment, the bone-engaging portion can be a ring-shaped member that is adapted to be positioned on a vertebral endplate. In yet another embodiment, the bone-engaging portion can be in the form of at least two inserts that are adapted to be implanted in a bone hole. The mating portion can be at least one connector that is mated to and extends between the at least two inserts.

The mating portion can also have a variety of configurations, but in one embodiment the mating portion can be in the form of a body having at least one cut-out formed therein and configured to receive a nucleus disc replacement implant for mechanically mating the mating portion to a nucleus disc replacement implant. The cut-out can be, for example, a groove formed around a perimeter of the body, a plurality of bores formed in the body, or other features formed on the body. In other embodiments, the mating portion can be in the form of a spiral-shaped body, and the bone-engaging portion can be formed on the opposed terminal ends of the spiral-shaped body. The spiral-shaped body can optionally include a plurality of pores formed therein and adapted to receive a nucleus disc replacement implant material.

In yet another embodiment, a nucleus disc replacement system is provided and includes an insert having a bone-engaging portion configured to engage an endplate of a vertebral body, and a mating portion configured to mate to a nucleus disc replacement implant, and a nucleus disc replacement implant adapted to be disposed within an annulus of a spinal disc and to mate to the mating portion of the insert. In certain embodiments, the system can include a plurality of inserts having a bone-engaging portion configured to engage an endplate of a vertebral body, and a mating portion configured to mate to a nucleus disc replacement implant.

While the configuration of the mating portion can vary, in one embodiment the mating portion can include at least one opening formed therein and configured to receive a portion of the nucleus disc replacement implant therein to mechanically interlock the insert and the nucleus disc replacement implant. In another embodiment, the mating portion can be at least one connector that is adapted to span between the bone-engaging portion of the plurality of inserts. The bone-engaging portion can also have various configurations, but in an exemplary embodiment the bone-engaging portion is adapted to penetrate an endplate of a vertebral body. For example, the bone-engaging portion can be in the form of a shank that is adapted to be disposed within a bone hole.

The nucleus disc replacement implant can also have various configurations, but in an exemplary embodiment it is formed from a material that is adapted to be injected into an annulus of a spinal disc.

Exemplary methods for replacing a nucleus are also provided. In one embodiment, the method can include removing a nucleus from within an annulus of a spinal disc positioned between opposed endplates of adjacent vertebrae. For example, the nucleus can be removed through an opening formed in the annulus of the spinal disc. A bone-engaging portion of at least one insert is mated to an endplate of at least one of the adjacent vertebrae to maintain the insert in a substantially fixed position. In one exemplary embodiment, the insert can be inserted through the opening formed in the annulus to position the insert within the annulus of the spinal disc. The method can also include inserting a nucleus disc replacement implant into the annulus of the spinal disc. The nucleus disc replacement implant can interact with at least a portion of the insert such that the insert prevents expulsion of the nucleus disc replacement implant. In an exemplary embodiment, the nucleus disc replacement implant mechanically interlocks with at least a portion of the insert. For example, the insert can include a mating portion that is positioned within the annulus and that interacts with the nucleus disc replacement implant. In one embodiment, the mating portion can have a height that is less than a height of a disc space formed between the adjacent vertebrae. Alternatively, the mating portion can have a height that is adapted to span across a disc space formed between the adjacent vertebrae such that the mating portion will maintain a height of the disc space.

In other aspects, mating a bone-engaging portion of an insert to an endplate can include penetrating the bone-engaging portion of the insert into the endplate. The mating portion is attached to the bone-engaging portion such that it is positioned within the annulus of the spinal disc. In other embodiments, mating a bone-engaging portion of at least one insert to an endplate of at least one of the adjacent vertebrae can include mating a bone-engaging portion of a first insert to an endplate of a first vertebra, and mating a bone-engaging portion of a second insert to an endplate of a second adjacent vertebra. The method can further include coupling the first and second inserts using at least one connector. The nucleus disc replacement implant can mechanically interlocking with the at least one connector.

BRIEF DESCRIPTION OF THE DRAWINGS

The invention will be more fully understood from the following detailed description taken in conjunction with the accompanying drawings, in which:

FIG. 1A is a perspective view of one exemplary embodiment of a nucleus disc replacement insert having a cylindrical mating portion;

FIG. 1B is a top view of the nucleus disc replacement insert of FIG. 1A;

FIG. 1C is a side view of the nucleus disc replacement insert of FIG. 1A;

FIG. 2A is a perspective view of another exemplary embodiment of a nucleus disc replacement insert having an ovular-shaped mating portion;

FIG. 2B is a top view of the nucleus disc replacement insert of FIG. 2A;

FIG. 2C is a side view of the nucleus disc replacement insert of FIG. 2A;

FIG. 3A is a perspective view of another exemplary embodiment of a nucleus disc replacement insert having a circular mating portion with openings formed therethrough;

FIG. 3B is a top view of the nucleus disc replacement insert of FIG. 3A;

FIG. 3C is a side view of the nucleus disc replacement insert of FIG. 3A;

FIG. 4A is a perspective view of another exemplary embodiment of a nucleus disc replacement insert having an ovular-shaped mating portion with pores formed therein;

FIG. 4B is a top view of the nucleus disc replacement insert of FIG. 4A;

FIG. 4C is a side view of the nucleus disc replacement insert of FIG. 4A;

DETAILED DESCRIPTION OF THE INVENTION

Figure 5C:
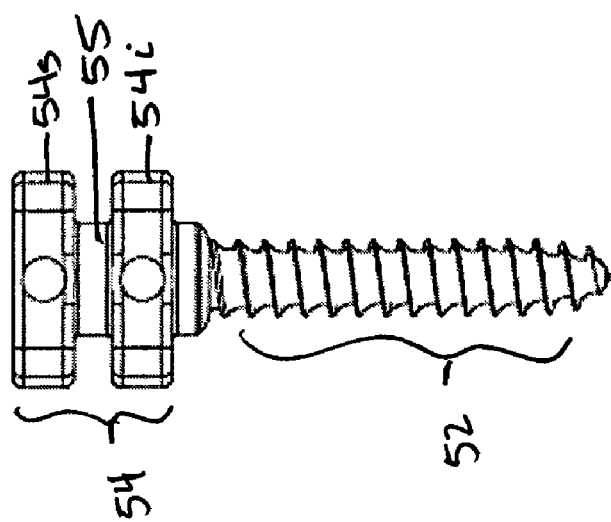
FIG. 5C is a side view of the nucleus disc replacement insert of FIG. 5A.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for replacing a nucleus of a spinal disc, and in particular for preventing nucleus disc replacement expulsion. The nucleus of a spinal disc can be removed from the annulus by forming a small opening in the annulus. Once the nucleus is removed, one or more insert devices can be implanted within the annulus of a spinal disc and they can be mated to one or both endplates of the adjacent vertebrae. The insert(s) is configured to interact with a nucleus disc replacement implant to prevent expulsion of the implant from the annulus. In particular, a nucleus disc replacement implant can be introduced into the annulus, preferably through the opening, to fill some or all of the annulus. The insert(s) and the nucleus disc replacement implant will interact such that the insert(s) will prevent the nucleus disc replacement implant from being expelled from the disc space, for example through the opening in the annulus. In certain exemplary embodiments, the interaction between the insert device(s) and the nucleus disc replacement can be mechanical to provide a secure mating connection between the nucleus disc replacement and the vertebra(e) to which the insert is attached. For example, the insert(s) can have a configuration that will allow a nucleus disc replacement implant that is introduced into the annulus of a spinal disc to be disposed around, to mate to, to adhere to, or to otherwise interlock with at least a portion of the insert.

While the various insert devices disclosed herein can be used with a variety of nucleus disc replacement implants, the nucleus disc replacement implant is preferably formed from a material that mimics the characteristics of a natural nucleus, and it preferably provides some or all of the resistance to compressive loads provided by a natural nucleus. In one exemplary embodiment, the nucleus disc replacement implant can be formed from a material that can be injected into the annular space defined by the annulus of the spinal disc. This will allow the material to surround and mate to the insert. While various nucleus disc replacement materials are known in the art, exemplary materials include, for example, hydrogels, silicones, polyurethanes, acrylics, collagens and adhesive (including cyanoacrylates and fibrin glue) that cures after being injected into the annulus of the disc. A person skilled in the art will appreciate that the nucleus disc replacement implant can be pre-shaped to mate to the insert and/or can be expanded, cured, and/or inflated prior to or after the introduction through the annulus.

FIGS. 1A-11 illustrate various exemplary insert devices that can be used to prevent expulsion of a nucleus disc replacement device. In general, each insert device includes a bone-engaging portion and a mating portion. The bone-engaging portion is preferably configured to mate to bone, such as an endplate of one or more vertebra, and the mating portion can be configured to be disposed within an annulus of a spinal disc and to interact with a nucleus disc replacement implant such that the mating portion prevents expulsion of the implant from the annulus. For example, the bone-engaging portion can be in the form of a shank having threads, ridges, or other bone-engaging surface features, a spike, a ring-shaped member, a wire, etc. The mating portion can also have various configurations, and can include features that facilitate mating with a nucleus disc replacement implant. For example, the mating portion can be in the form of a body having pores, openings, grooves, etc., and/or having an asymmetrical shape, such as a spiral or ring shape. The mating portion can also optionally have an expandable or spring-type configuration. In other embodiments, the mating portion can be formed from several wires or strings, or from a mesh material that allows the nucleus disc replacement implant to interact therewith. A person skilled in the art will appreciate that the particular configuration of the insert can vary, and that FIGS. 1A-11 merely illustrate various exemplary embodiments.

Turning first to FIG. 1A-1C, one exemplary embodiment of an insert 10 is shown having a bone-engaging portion that is in the form of a shank 12, and a mating portion that is in the form of a head 14 disposed on the shank 12. In general, the shank 12 includes threads 12a formed thereon for engaging bone to allow the shank 12 to be threaded into a bone hole. In use, the shank 12 can be implanted in an endplate of a vertebra to allow the head 14 to be positioned within the annulus of a spinal disc. While threads 12a are shown, a person skilled in the art will appreciate that the shank 12 can include various other bone-engaging surface features, such as ridges, teeth, a stepped configuration, etc. The head 14 of the insert 10 has a generally cylindrical configuration and includes opposed superior and inferior surfaces 14s, 14i and a sidewall 14c extending therebetween. The shank 12 is mated to and extends distally from the inferior surface 14i of the head 14. The head 14 also includes a cut-out or groove 16 formed around a perimeter of the sidewall 14c. The cut-out or groove 16 will facilitate interaction between the nucleus disc replacement implant and the insert 10. In particular, when the nucleus disc replacement implant is injected into the annular space defined by the annulus of the spinal disc, the implant can surround the head 14 of the insert 10, filling the space defined by the groove 16. As a result, when the nucleus disc replacement implant cures it will be mechanically interlocked with the head 14. The head 14 therefore prevents expulsion of the implant from the annulus of the spinal disc.

The particular size of the head 14 can also vary. For example, the head 14 can have a height that is less than a height extending between adjacent vertebrae, i.e., that is less than a height of the disc space. Alternatively, the head 14 can have a height that is only slightly less than a height of the disc space such that the head 14 provides a mechanical stop during movement of the adjacent vertebrae. In other embodiments, the head 14 can have a height that spans across and is substantially equal to a height of the disc space such that the head 14 functions as a load bearing surface. The head 14 can also have an extend, i.e., a diameter or width, that varies. In certain exemplary embodiments, the head 14 has a size and shape that is less than a size of the annular space defined by the annulus. This will allow room for the nucleus disc replacement implant to be introduced into the annulus. A person skilled in the art will appreciate that that various other insert embodiments disclosed and discussed herein can also have shapes and sizes that vary to obtain the desired result during use. The various inserts disclosed herein can also be formed from various materials, and they can be rigid or flexible.

FIGS. 2A-2C illustrate another embodiment of an insert 20. In this embodiment, the insert 20 is similar to the insert 10 of FIGS. 1A-1C and generally includes a shank 22 and a head 24 formed on or mated to the shank 22. In this embodiment, however, the head 24 has a substantially planar configuration and is oblong or ovular in shape. The asymmetrical shape of the head 24 can help facilitate the mechanical mating connection between the insert 20 and a nucleus disc replacement implant. The planar head 24 will also allow the annulus to be mainly occupied by the nucleus disc replacement implant, rather than the head 24 of the insert 20.

FIGS. 3A-3C illustrate yet another embodiment of an insert 30 that is similar to the inserts 10, 20 of FIGS. 1A-2C and generally includes a shank 32 and a head 34 formed on or mated to the shank 32. In this embodiment, the insert 30 has a planar head 34 with a circular configuration. The head 34 includes several opening 36 formed therein and extending between superior and inferior surfaces 34s, 34i thereof. The openings 36 allow the nucleus disc replacement implant to flow therein thus providing a secure mechanical interlock between the nucleus disc replacement implant and the insert 30.

In another embodiment, shown in FIGS. 4A-4C, the head 44 of the insert 40 includes a combination of surface features to facilitate interaction between the nucleus disc replacement implant and the insert 40. In particular, the head 44 has a generally ovular configuration with opposed superior and inferior surfaces 44s, 44i that are connected by a sidewall 44c. Several grooves 46 are formed around a perimeter of the sidewall 44c and along the superior surface of the head 44. The head 44 further includes several openings or bores 48 formed in various portions thereof. In the illustrated embodiment, the bores 48 are formed around the sidewall 44*c* and in the superior surface 44*s*. In use, the nucleus disc replacement implant will flow into the grooves 46 and the bores 48, and will cure to form a mechanical interlock with the head 44 of the insert 40. As further shown, the insert 40 also includes a shank 42 extending from the inferior surface 44*i* of the head 44. As with the previous embodiments, while a shank is shown other bone-engaging elements can be used.

Figure 5B:
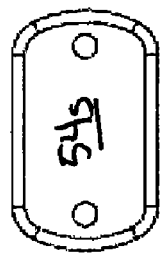
FIG. 5B is a top view of the nucleus disc replacement insert of FIG. 5A.
Figure 5A:
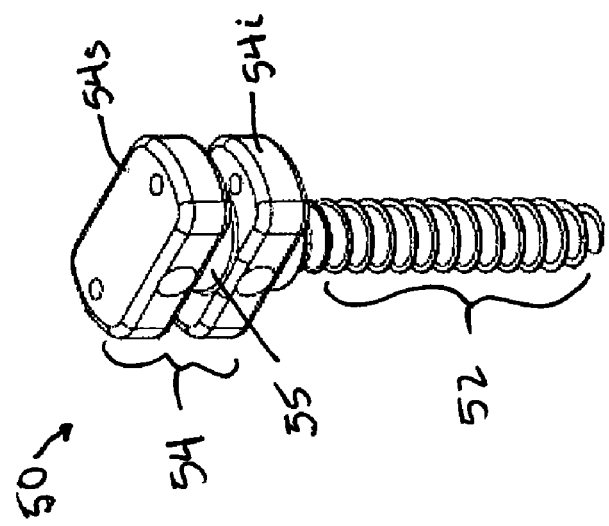
FIG. 5A is a perspective view of another exemplary embodiment of a nucleus disc replacement insert having a mating portion that is adapted to provide a mechanical stop during movement of adjacent vertebrae.

In another embodiment, shown in FIGS. 5A-5C, the insert 50 can have an elongate head 54 that is adapted to provide a mechanical stop during movement of adjacent vertebrae, or that can function as a load bearing surface during movement of adjacent vertebrae. In general, the insert 50 includes a shank 52 with a head 54 formed thereon or mated thereto. The shank 52 is similar to the shank 12 of FIGS. 1A-1C, however other bone-engaging members can be used instead of a shank. The head 54 includes superior and inferior members or plates 54*s*, 54*i*, each having a generally rectangular configuration. The plates 54*s*, 54*i* are mated to one another by a central portion 55 that is positioned therebetween and that maintains the plates 54*s*, 54*i* at a fixed distance apart from one another. The central portion 55 has a width and length that is less than a width and length of each plate 54*s*, 54*i*, such that a groove or opening is formed around the central portion 55 and between the plates 54*s*, 54*i*.

Figure 6:
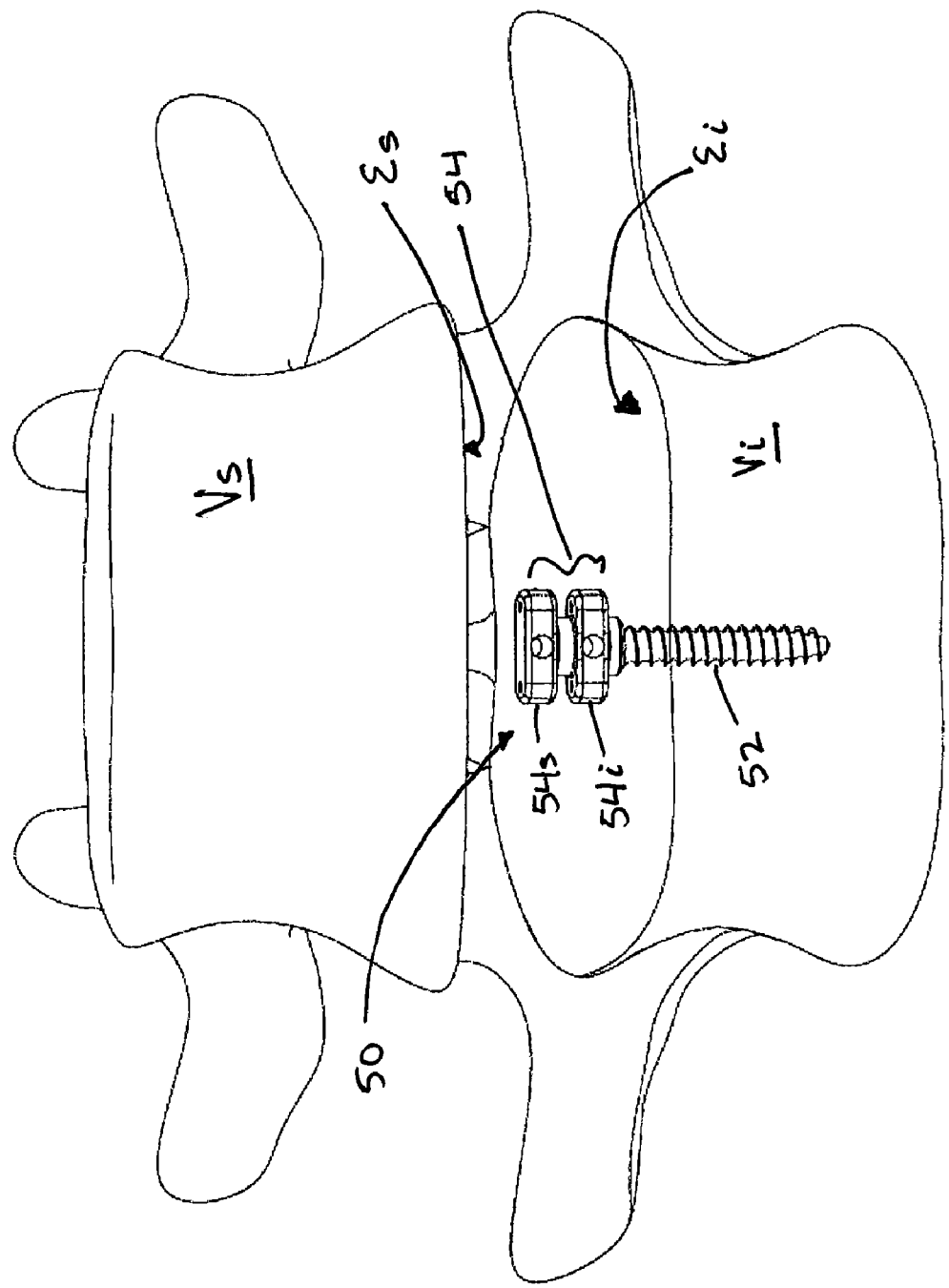
FIG. 6 is a side view of the insert of FIG. 5A implanted between adjacent vertebrae.

In use, as shown in FIG. 6, the shank 52 can be implanted in a vertebra, such as an inferior vertebra $V_i$ as shown, to position the head 54 within a space defined by the annulus (not shown) of a spinal disc. The inferior plate 54*i* can be positioned adjacent to, i.e., in contact with or spaced a distance apart from, the endplate $E_i$ of the inferior vertebra $V_i$, and the superior plate 54*s* can be positioned adjacent to, i.e., in contact with or spaced a distance apart from, the endplate $E_s$ of an adjacent superior vertebra $V_s$. During movement of the adjacent vertebra $V_s$, $V_i$, the plates 54*s*, 54*i* can provide a mechanical stop to limit flexion, extension, etc. of the adjacent vertebrae $V_s$, $V_i$. Alternatively, where the height of the head 54 is substantially equal to the height of the disc space, the plates 54*s*, 54*i* will be positioned in contact with the endplates $E_s$, $E_i$, of the vertebrae $V_s$, $V_i$ to prevent movement of the adjacent vertebrae, or to at least function as a load bearing surface during movement. For example, the head 54 can be formed from a compressible material, and/or the central portion 55 can allow movement between the plates 54*s*, 54*i*, to help control movement of the adjacent vertebrae $V_s$, $V_i$.

Figure 7A:
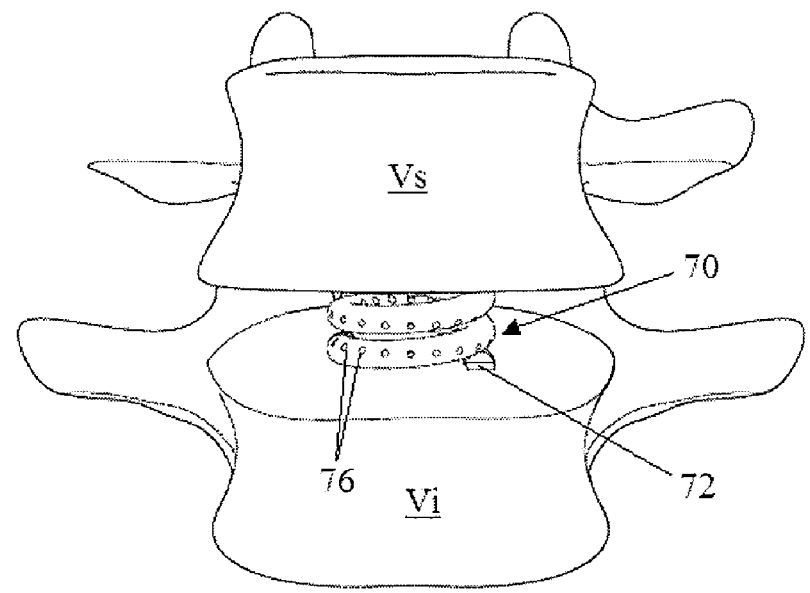
FIG. 7A is a side view of adjacent vertebrae having a spiral-shaped insert implanted therebetween in accordance with another embodiment of the present invention.

As previously mentioned, the insert can also have various other configurations. For example, the bone-engaging portion of the insert can be adapted to engage an endplate using a friction fit. By way of non-limiting example, the insert can be formed from a shape-memory material, can have a spring-type configuration, a balloon configuration, or another mechanical configuration that provides a friction fit between the endplates. FIG. 7A illustrates one embodiment of an insert 70 in the form of a coil spring. The coil spring insert 70 includes a first end 72 that can mate or engage an endplate of a first vertebrae $V_i$, and a second end (not shown) that can mate to or engage an endplate of a second adjacent vertebrae $V_s$. Various mating techniques can be used to mate the ends of the insert 70 to the endplates of the vertebrae $V_s$, $V_i$. For example, the ends can include bone-penetrating members formed thereon, such as spikes, teeth, etc. Alternatively, the ends can engage the endplates due to the configuration of the insert 70. That is, the coil spring can be sized to retain the insert 70 between the adjacent vertebrae by a compression fit or a mechanical friction fit, such that the ends merely abuts against and engage the endplates without penetrating the endplates.

Figure 7B:
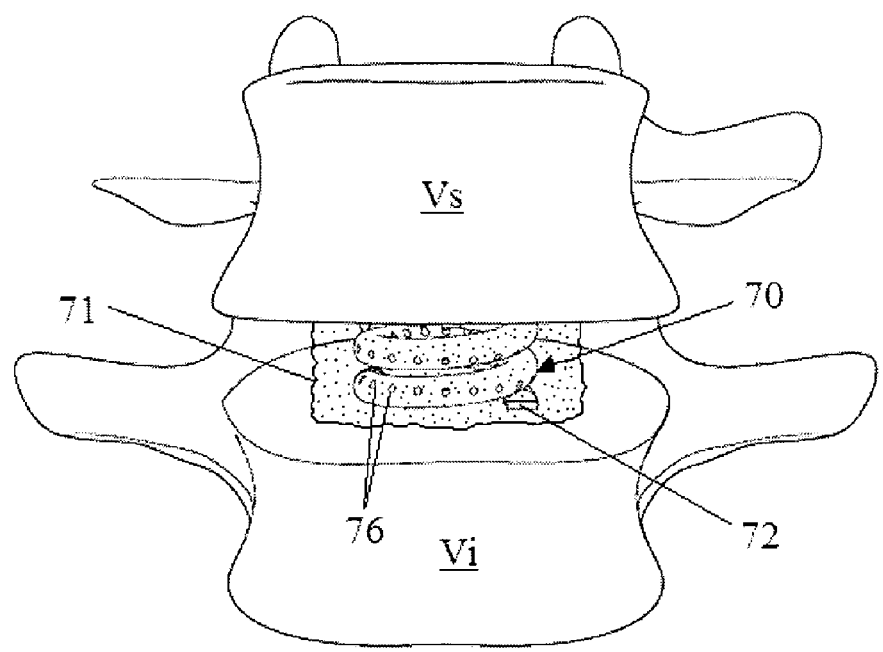
FIG. 7B is a side view of the adjacent vertebrae and spiral-shaped insert of FIG. 7A having a nucleus disc replacement implant surrounding the spiral-shaped insert.

The body of the insert 70 extending between the ends can also have various configurations, for example it can be in the form of a solid or hollow coil. The coil configuration can facilitate mechanical mating of a nucleus disc replacement implant 71 thereto, as shown in FIG. 7B, and it can also provide a load bearing member during movement of the adjacent vertebrae $V_s$, $V_i$. For example, the coil can compress to provide resistance to extension and lateral bending of the adjacent vertebrae $V_s$, $V_i$. As shown in FIGS. 7A and 7B, the coiled body can also optionally include one or more bores or openings 76 formed therein and configured to receive the nucleus disc replacement implant 71 to further facilitate mating of the implant 71 to the insert 70.

Figure 9A:
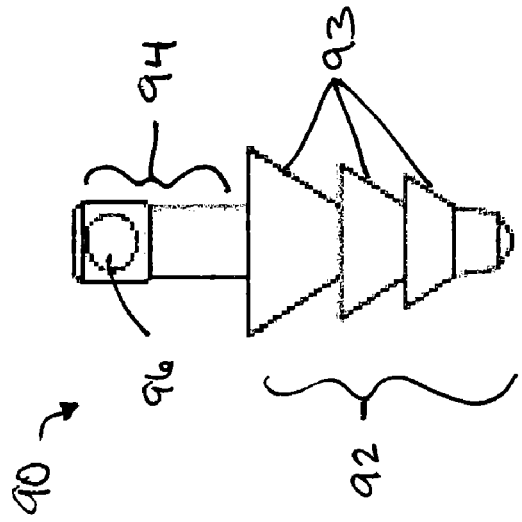
FIG. 9A is a side view of yet another embodiment of a nucleus disc replacement insert having a shank with a stepped configuration for engaging bone.
Figure 8:
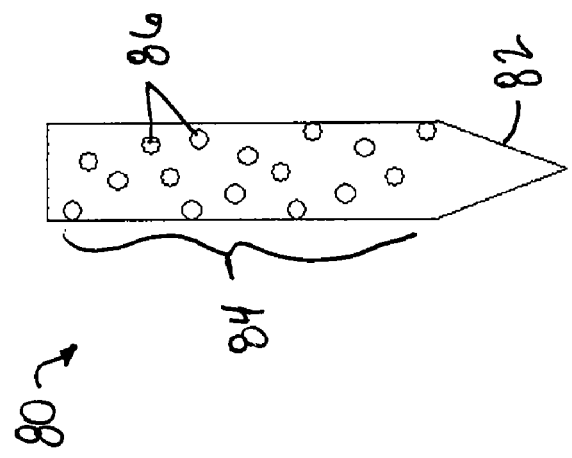
FIG. 8A is a side view of yet another embodiment of a nucleus disc replacement insert in the form of a spike-shaped member.
Figure 9B:
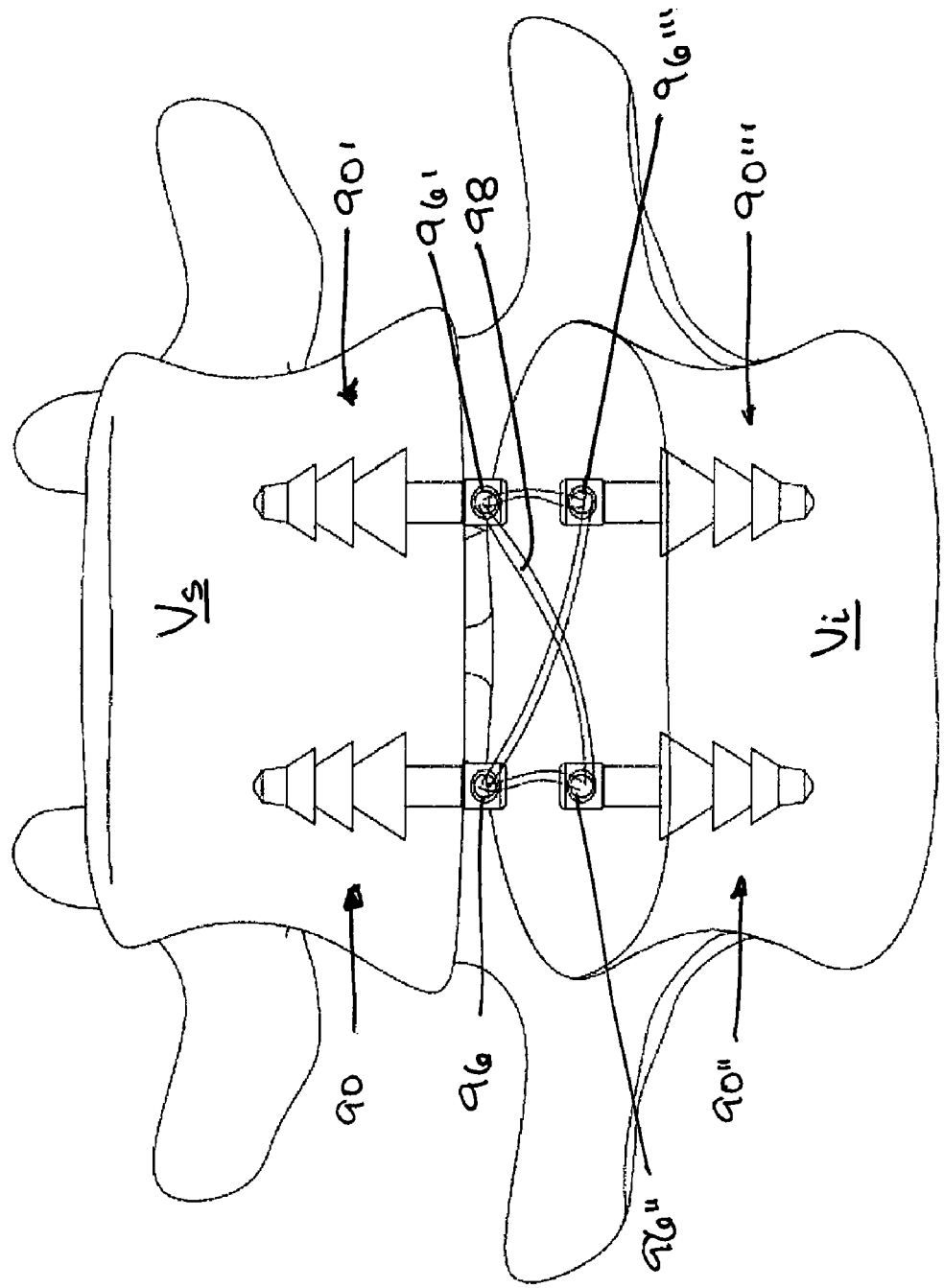
FIG. 9B is a side view of four of the inserts of FIG. 9A implanted in adjacent vertebrae and having a connector extending therebetween in accordance with yet another embodiment of the present invention.

FIGS. 8 and 9A illustrate various other insert configurations. In the embodiment shown in FIG. 8, the insert 80 is in the form of a spiked shank having a pointed or sharp distal bone-engaging portion 82 that is configured to penetrate into bone, and a proximal mating portion 84 for mating with a nucleus disc replacement implant. The mating portion 84 is shown having a plurality of openings or bores 86 formed therein for receiving the nucleus disc replacement implant. In another embodiment, shown in FIG. 9A, the insert 90 can include ridges 93 formed on a distal bone-engaging portion 92 and having a stepped configuration to facilitate mating of the bone-engaging portion 92 with bone. The insert 90 can also include a proximal mating portion 94 that is in the form of a shank and that includes a bore 96 formed therethrough in a terminal end thereof. The bore 96 can be used to receive the nucleus disc replacement material, or alternatively it can be used to mate to a connector that is adapted to span across the annular space. By way of non-limiting example, FIG. 9B illustrates four inserts 90, 90', 90", 90''' implanted in adjacent vertebrae $V_s$, $V_i$. The inserts 90, 90', 90", 90''' are connected to one another by a wire or string connector 98 that is threaded through the bore 96, 96', 96", 96''' formed in each insert 90, 90', 90", 90'''. As a result, when a nucleus disc replacement material is injected into the annulus, the material will fill the space around and between the string or wire 98, and will cure to form a mechanical interlock with the string or wire 98, as well as with the mating portion of the insert 90, 90', 90", 90'''. The connector 98 and the inserts 90, 90', 90", 90''' will thus prevent the nucleus disc replacement implant from being expelled from the annular space. In other embodiments, rather than using a wire or string connector 98, the connector can be in the form of a mesh material, such as a flexible mesh bag, that allows the nucleus disc replacement implant to flow therein and interlock therewith, or from similar materials such as a floss, string, or other flexible and/or porous material.

Figure 10:
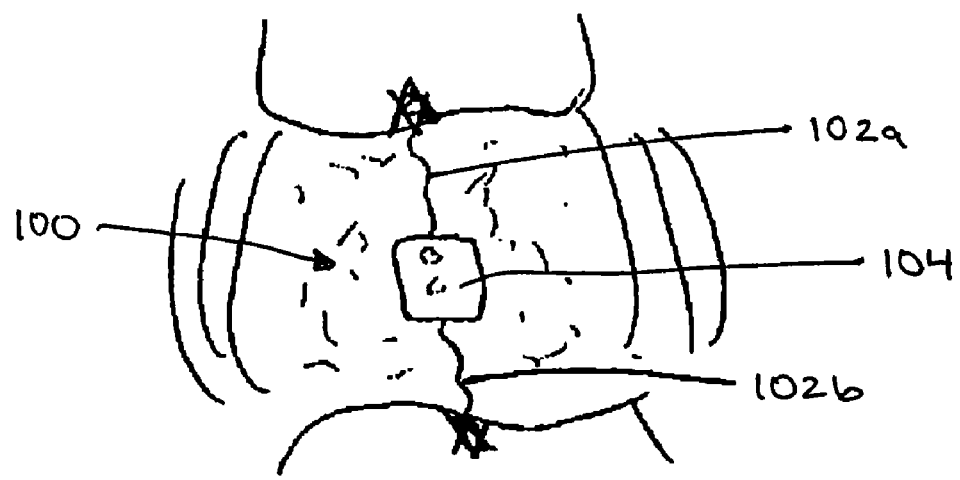
FIG. 10 is a side view of another embodiment of an insert having a mating portion and bone-engaging portions extending from opposed sides of the mating portion and mated to adjacent vertebrae.
Figure 11:
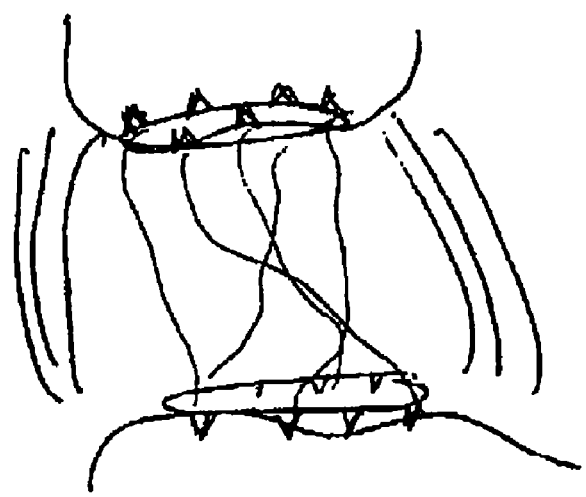
FIG. 11 is a side view of yet another embodiment of an insert having ring-shaped mating portion mated to adjacent vertebrae, and one or more connectors extending therebetween.

FIGS. 10-11 illustrate various other embodiments of inserts that utilize a connector. In the embodiment shown in FIG. 10, the insert 100 includes a mating portion 104 that is configured to be positioned within the annulus of a spinal disc, and first and second bone-engaging portions 102*a*, 102*b* that extend from the mating portion 104 and that each mate to an endplate of a vertebra. The particular configuration of the mating portion 104 can vary, however FIG. 10 illustrates a generally rectangular body having one or more openings formed therein for receiving the nucleus disc replacement implant. The bone-engaging portions 102*a*, 102*b* can also vary, and they can be formed from string or wires, or in other embodiments they can be elastic and/or compressible. For example, the bone-engaging portions 102*a*, 102*b* can each be in the form of a Nitinol wire or a spring member that provides some resistance to movement of the adjacent vertebrae. In another embodiment, shown in FIG. 11, the insert 110 can include a first bone-engaging member 102a that mates to an endplate of a first vertebra, e.g., a superior vertebra $V_s$, and a second bone-engaging member 102b that mates an endplate of a second vertebra, e.g., an inferior vertebra $V_i$. Each bone-engaging member 102a, 102b can be in the form of a ring-shaped body having bone-engaging surface features, such as teeth, formed thereon for engaging the endplates. The insert 110 can also include one or more connectors 104 extending between the bone-engaging members 102a, 102b such that the connectors 104 span across the annular space. As shown in FIG. 11, the connector 104 is in the form of a string or wire that is wrapped around each bone-engaging member 102a, 102b several times. In use, the connector 104 will facilitate mating of the nucleus disc replacement implant thereto to prevent expulsion of the implant.

A person skilled in the art will appreciate that the various features of the various exemplary insert devices disclosed herein can be used in any combination with one another, and that the inserts can have a variety of other configurations to facilitate mating to bone and mating to a nucleus disc replacement implant. Use of the inserts can also vary, and they can be used individually or they can be used in various combinations in conjunction with one another. For example, multiple inserts can be disposed within the same annulus to provide for multiple attachment points for a nucleus disc replacement implant.

In other embodiments, either the insert or nucleus disc replacement implant can be treated to improve attachment to the each other or to the bone. For example, one or both bone-engaging portions of the insert can be treated to facilitate bony attachment and the mating portion can be treated to facilitate attachment to the nucleus disc replacement device. The treatment(s) can be mechanical or chemical. In the case of bony attachment the bone-engaging portion can also or alternatively include mechanical surface features to provide for bony fixation and/or ingrowth. This feature can be roughed texture, an attached mesh, a beaded surface, etc. Exemplary chemical agents include, by way of non-limiting example, hydroxyapatities, phosphates, and the like for improving bony integration.

Attachment to the nucleus disc replacement device can also optionally be enhanced with the use of pretreatments. These pretreatments can also be mechanical or chemical. In one embodiment, mating portion of the insert can be treated to provide an increased surface area of surface features for nucleus disc replacement attachment via mechanical means. Conversely, the mating portion can be treated to improve attachment by chemical means, for example, by providing surfactants or primers to improve wetability as well as adhesives to improve bonding. The adhesives can be formulated to provide covalently bonded attachment locations with injectable nucleus implants.

The present invention also provides various exemplary methods for replacing a nucleus of a spinal disc. In one exemplary embodiment, the nucleus can be replaced by forming a small opening in the annulus of a spinal disc and removing a portion or all of the natural nucleus. Various techniques are known in the art and can be used for forming an opening and removing the nucleus. Once the space within the annulus is prepared, one or more inserts can be introduced either sequentially or simultaneously in the annular space and can be mated to one or both endplates of the adjacent vertebrae. In an exemplary embodiment, the insert is introduced through the opening previously formed in the annulus. To allow this to be done, the insert preferably has a size and shape that is less than a size of the annular space, and more preferably that is less than the size of the opening to allow the insert to fit through the opening. Once the insert is positioned within the annular space, the bone-engaging portion can be mated to one or both endplates. For example, where the insert includes a threaded shank or a shank with ridges, that shank can be threaded directly into the bone or it can be inserted into a pre-drilled bone hole formed in the endplate. When the bone-engaging portion is mated to the vertebra, the mating portion of the insert will be retained within the annular space to allow it to mate to a nucleus disc replacement implant. In other embodiments, rather than introducing the insert through the annulus, the insert can be introduced through a bone hole formed in a vertebra. For example, a tunnel can be drilled from a sidewall of a vertebrae diagonally toward an endplate of the vertebra to provide access to the annular space, and the insert can be introduced therethrough. The bone-engaging portion can mate to the bone hole or to another portion of the vertebra to maintain the mating portion within the annular space.

Once the insert is positioned within the annulus and is anchored to one or both vertebrae surrounding the annulus, a nucleus disc replacement implant can be introduced into the annular space. In an exemplary embodiment, the nucleus disc replacement implant is in the form of a material that is injected into the annular space and that expands in situ to surround the mating portion of the insert. The nucleus disc replacement implant will thus cure to form a mechanical mating connection with the insert, and thus the insert will anchor the nucleus disc replacement implant to the vertebra (e) to prevent expulsion. A person skilled in the art will appreciate that the order of steps can vary, and that the order can be reversed or can otherwise differ from the procedure discussed above. For example, the nucleus replacement can be inserted into the disc space first, and then the vertebral insert can be introduced.

Figure 12:
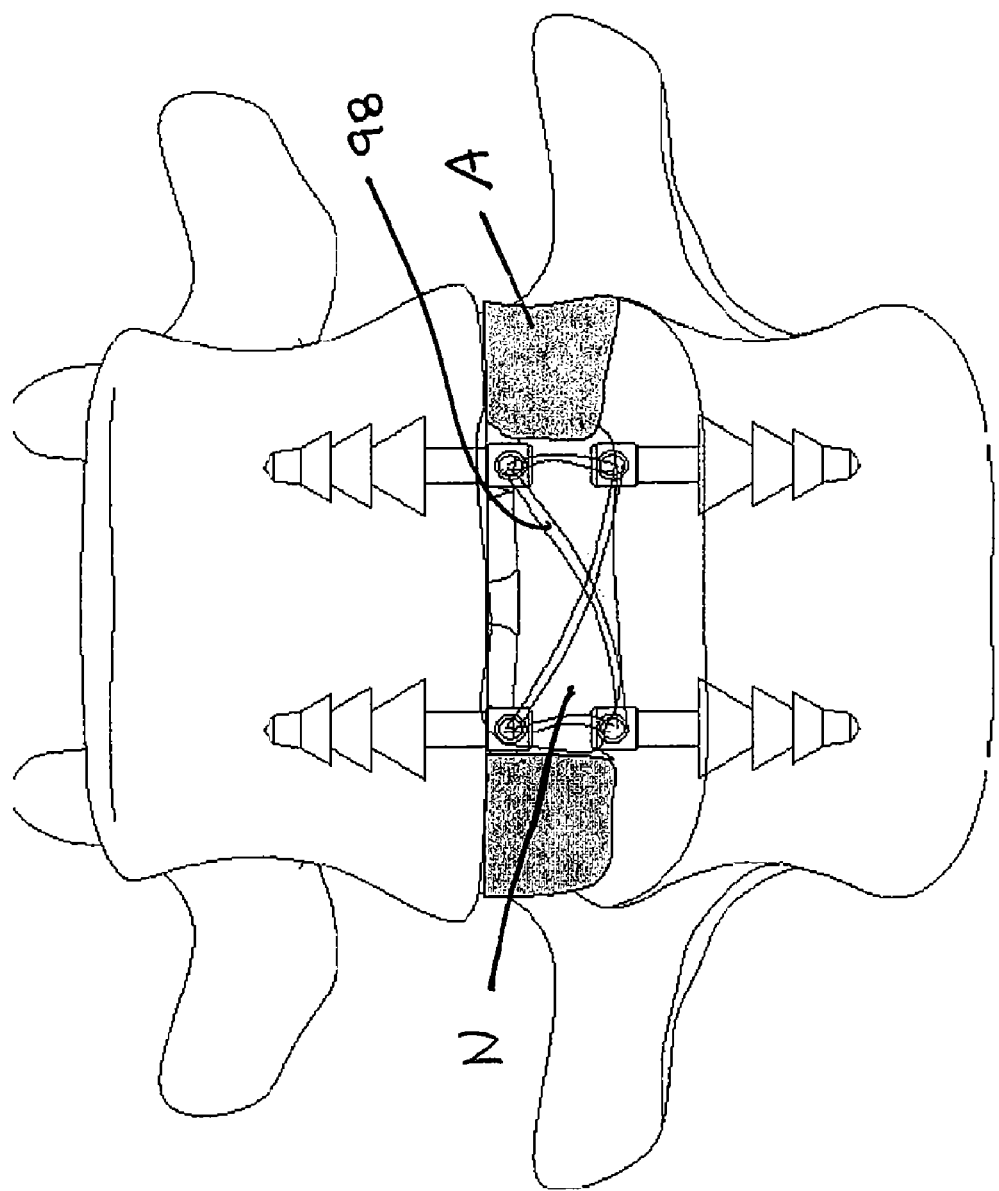
FIG. 12 is a side view of the inserts and vertebrae of FIG. 9B showing the annulus of a disc and showing a nucleus disc replacement implant disposed therein and mated to the connector.

By way of non-limiting example, FIG. 12 illustrates the insert system of FIG. 9B having the annulus A surrounding the annular space, and having a nucleus disc replacement implant N disposed around and mated to the connector 98 such that the connector 98 prevents expulsion of the nucleus disc replacement implant N. While not necessary, the opening previously formed in the annulus can optionally be closed after the procedure is completed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A vertebral body insert system, comprising:
   a coiled insert body having bone-engaging terminal ends configured to engage bone to maintain the insert body in a substantially fixed position relative to the bone, and a mating portion having a sidewall with a plurality of pores formed therein, the mating portion being adapted to mate with a nucleus implant, and the mating portion being sized and shaped for positioning within an annular space defined by an annulus of a spinal disc such that the mating portion has a size that is less than a size of the annular space; and a nucleus disc replacement implant configured to be injected into an annulus of a spinal disc and to surround the mating portion and extend into the plurality of pores in the mating portion such that the coiled insert body is configured to retain the nucleus disc replacement member within the annulus.

2. The system of claim 1, wherein the bone-engaging ends are adapted to frictionally engage an endplate of a vertebral body.

3. The system of claim 1, wherein the bone-engaging ends are adapted to penetrate an endplate of a vertebral body.

4. The system of claim 1, wherein the plurality of pores are adapted to receive a nucleus disc replacement implant material therein.

5. The system of claim 1, wherein at least a portion of the insert body is formed from a material selected from the group consisting of a mesh, a net, a floss, a string, and a porous material.

6. The system of claim 1, wherein the mating portion of the coiled insert body is hollow.

7. The system of claim 6, wherein the plurality of openings are adapted to receive the nucleus implant.

8. The system of claim 1, wherein the coiled insert body is configured to compress to provide resistance to extension of adjacent vertebrae.

9. A vertebral body insert system, comprising:
a coiled insert body having bone-engaging terminal ends configured to engage adjacent vertebrae to maintain the insert body in a substantially fixed position relative to the vertebrae, and a mating portion having a sidewall with a plurality of pores formed therein, the mating portion being adapted to mate with a nucleus implant, and the mating portion being sized and shaped for positioning within an annular space defined by an annulus of a spinal disc such that the mating portion has a size that is less than a size of the annular space, wherein the mating portion is adapted to compress and expand to allow adjacent vertebrae to move relative to one another; and
a nucleus disc replacement implant configured to be injected into an annulus of a spinal. disc and to surround the mating portion and extend into the plurality of pores in the mating portion such that the coiled insert body is configured to retain the nucleus disc replacement member within the annulus.

10. The system of claim 9, wherein the plurality of openings are adapted to receive the nucleus implant.

11. The system of claim 9, wherein the coiled insert body has at least two successive turns.

* * * * *